US008871980B2

(12) United States Patent
Sajiki et al.

(10) Patent No.: US 8,871,980 B2
(45) Date of Patent: Oct. 28, 2014

(54) PROCESS FOR PRODUCING HYDROGEN OR HEAVY HYDROGENS, AND HYDROGENATION (PROTIATION, DEUTERATION OR TRITIATION) OF ORGANIC COMPOUNDS USING SAME

(75) Inventors: Hironao Sajiki, Gifu (JP); Yasunari Monguchi, Gifu (JP); Yoshinari Sawama, Gifu (JP); Shinichi Kondo, Aichi (JP)

(73) Assignee: Shiono Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/817,637

(22) PCT Filed: Aug. 16, 2011

(86) PCT No.: PCT/JP2011/068535
§ 371 (c)(1),
(2), (4) Date: Feb. 19, 2013

(87) PCT Pub. No.: WO2012/023546
PCT Pub. Date: Feb. 23, 2012

(65) Prior Publication Data
US 2013/0150623 A1    Jun. 13, 2013

(30) Foreign Application Priority Data

Aug. 18, 2010 (JP) ................................. 2010-182826

(51) Int. Cl.
| B01J 31/00 | (2006.01) |
| B01J 37/00 | (2006.01) |
| C08F 4/02 | (2006.01) |
| C08F 4/60 | (2006.01) |
| C07C 209/00 | (2006.01) |
| C07C 45/61 | (2006.01) |
| C07C 41/24 | (2006.01) |
| C07C 41/26 | (2006.01) |
| C01B 3/08 | (2006.01) |
| C07B 35/02 | (2006.01) |
| C01B 4/00 | (2006.01) |
| C07C 29/17 | (2006.01) |
| C07B 35/06 | (2006.01) |
| C07C 5/10 | (2006.01) |
| C07C 221/00 | (2006.01) |
| C07C 29/143 | (2006.01) |
| C07C 213/02 | (2006.01) |
| C07B 59/00 | (2006.01) |
| C07C 209/36 | (2006.01) |
| C07C 1/26 | (2006.01) |
| C07C 5/09 | (2006.01) |
| C07B 31/00 | (2006.01) |
| C07C 41/20 | (2006.01) |

(52) U.S. Cl.
CPC . *C01B 4/00* (2013.01); *C07C 45/61* (2013.01); C07B 2200/05 (2013.01); *C07C 41/24* (2013.01); *C07C 41/26* (2013.01); *C01B 3/08* (2013.01); *C07B 35/02* (2013.01); *C07C 29/17* (2013.01); C07C 2101/14 (2013.01); *C07B 35/06* (2013.01); *C07C 5/10* (2013.01); *C07C 221/00* (2013.01); C07C 2523/745 (2013.01); *C07C 29/143* (2013.01); *C07C 213/02* (2013.01); *C07B 59/00* (2013.01); Y02E 60/364 (2013.01); *C07C 209/36* (2013.01); *C07C 1/26* (2013.01); *C07C 5/09* (2013.01); *C07B 31/00* (2013.01); *C07C 41/20* (2013.01)
USPC ............................ 564/398; 564/421; 502/103

(58) Field of Classification Search
None
See application file for complete search history.

(56) References Cited

U.S. PATENT DOCUMENTS

| 2,056,822 | A | * | 10/1936 | Britton et al. | ............. | 260/665 G |
| 3,132,188 | A | * | 5/1964 | Cook | ............................ | 585/469 |
| 6,334,583 | B1 | * | 1/2002 | Li | ................................ | 241/175 |
| 6,382,537 | B1 | | 5/2002 | Birke | | |

FOREIGN PATENT DOCUMENTS

| CN | 101028921 | 9/2007 |
| JP | 2001 517641 | 10/2001 |
| JP | 2005 170780 | 6/2005 |
| JP | 2005-248027 | 9/2005 |
| JP | 2007 31169 | 2/2007 |
| JP | 2010 120825 | 6/2010 |

OTHER PUBLICATIONS

Ramnial et al. "Grignard Reagents in Ionic Solvents: ET Reactions and Evidence for Facile Br/Mg Exchange", Chemical Communications 2007, supplementary material, pp. 1-9.*
March, J. Organic Chemistry: Reactions, Mechanisms and Structure; 4th edition, 1992, front matter and pp. 567-577.*
Retsch brochure, "Size Reduction with Planetary Ball Mills", 2009, pp. 1-12.*
International Search Report Issued Nov. 22, 2011 in PCT/JP11/68535 Filed Aug. 16, 2011.

* cited by examiner

Primary Examiner — Clinton Brooks
(74) Attorney, Agent, or Firm — Oblon, Spivak, McClelland, Maier & Neustadt, L.L.P.

(57) ABSTRACT

An object is to provide a process for providing hydrogen or heavy hydrogens conveniently without the necessity of large-scale equipment and a process capable of performing hydrogenation (protiation, deuteration or tritiation) reaction conveniently without the use of an expensive reagent and a special catalyst. The production process includes a process for producing hydrogen or heavy hydrogens, containing subjecting water or heavy water to mechanochemical reaction in the presence of a catalyst metal, and a process for producing a hydrogenated (protiated, deuterated or tritiated) organic compound, containing subjecting an organic compound and water or heavy water to mechanochemical reaction in the presence of a catalyst metal.

13 Claims, No Drawings

US 8,871,980 B2

PROCESS FOR PRODUCING HYDROGEN OR HEAVY HYDROGENS, AND HYDROGENATION (PROTIATION, DEUTERATION OR TRITIATION) OF ORGANIC COMPOUNDS USING SAME

CROSS REFERENCE TO RELATED APPLICATIONS

The present application is a 35 U.S.C. §371 national stage patent application of International patent application PCT/JP2011/068535, filed on Aug. 16, 2011, published as WO/2012/023546 on Feb. 23, 2012, the text of which is incorporated by reference, and claims the benefit of the filing date of Japanese application no. 2010-182826, filed on Aug. 18, 2010, the text of which is also incorporated by reference.

TECHNICAL FIELD

The present invention relates to a process for producing hydrogen or heavy hydrogens (deuterium and tritium) by utilizing mechanochemical reaction, and hydrogenation (protiation, deuteration or tritiation) of an organic compound using the same.

BACKGROUND ART

Hydrogen has been utilized in various fields in industry. Specifically, hydrogen has been used as raw materials, for example, in production of ammonia by the Haber-Bosch process, production of hydrochloric acid by photoreaction with chlorine gas, and modification of oil and fat, such as corn oil and cotton oil, by adding hydrogen thereto for hydrogenation (hardening), and as reducing agents, for example, in reduction of metallic minerals (oxides), production of aniline by reducing nitrobenzene, catalytic reduction of benzene in production of nylon 66, synthesis of methyl alcohol by reducing carbon monoxide, and desulfurization.

Furthermore, hydrogen does not form wastes, such as particulate emissions and exhaust gas, e.g., carbon dioxide, other than water on combustion, and thus is being expected as alternate energy. A hydrogen-fueled car having a hydrogen-fueled engine as an internal combustion engine is commercially available, and hydrogen is used as a rocket fuel and in a fuel cell.

Hydrogen is mass-produced industrially as a by-product of steam reformation and partial oxidation of a hydrocarbon (i.e., the hydrocarbon gas decomposition method). In the method, methane gas in natural gas, paraffin compounds, ethylene or propylene is decomposed into hydrogen and carbon monoxide by reacting with steam with nickel as a catalyst at a high temperature, and carbon monoxide thus by-produced is further reacted with steam to form carbon dioxide and hydrogen gas. As an alternate method, such hydrogen may be utilized that is formed as a by-product of electrolysis of seawater in soda industry and salt production.

Hydrogenation reaction where hydrogen is reacted with an organic compound is being widely used in organic synthetic chemistry, and various useful compounds are formed by the method. Various types of hydrogenation reaction have been known, such as reaction utilizing an alkali metal or the like, reaction utilizing a metal hydride or a metal hydrogen complex, reaction utilizing diborane or hydrazine, reaction utilizing catalytic hydrogenation, and the like.

However, the industrial production methods of hydrogen described above require large-scale equipment and cannot be utilized for convenient production of hydrogen gas. There is an experimental method of utilizing hydrogen gas that is generated by dissolving a metal in a diluted acid or an alcohol, but the method has problems in that a metal is irreversibly dissolved, and a solution formed by dissolving a metal is necessarily treated.

Furthermore, in the hydrogenation reactions described above, the methods using an alkali metal, a metal hydride, a metal hydrogen complex, diborane and hydrazine have a problem of high cost of the reagents used and a problem of risks of the reagents. The method utilizing catalytic hydrogenation also has a problem in that a special metal catalyst is necessarily used.

SUMMARY OF THE INVENTION

Problems to be Solved by the Invention

The present invention has been made under the circumstances, and an object thereof is to provide a process for providing hydrogen conveniently without the necessity of large-scale equipments, and a process for performing hydrogenation reaction conveniently without the use of an expensive reagent and a special catalyst.

Means for Solving the Problems

The present inventors, who have performed various experiments relating to organic synthesis reaction, have found that reaction of an organic compound and water in a particular reaction system hydrogenates the organic compound. Furthermore, the inventors have found that the reaction performed only with water forms hydrogen gas. Moreover, the inventors have confirmed that deuteration of an organic compound and formation of deuterium gas may also be performed when heavy water is used instead of water, and thus the present invention has been completed.

The present invention relates to a process for producing hydrogen or heavy hydrogens, containing subjecting water or heavy water to mechanochemical reaction in the presence of a catalyst metal.

The invention also relates to a process for producing a hydrogenated (protiated, deuterated or tritiated) organic compound, containing subjecting an organic compound and water or heavy water to mechanochemical reaction in the presence of a catalyst metal.

The invention further relates to a process for hydrogenating (protiating, deuterating or tritiating) an organic compound, containing subjecting an organic compound and water or heavy water to mechanochemical reaction in the presence of a catalyst metal.

The invention further relates to a process for dehalogenating an organic compound containing halogen, containing subjecting an organic compound containing halogen and water or heavy water to mechanochemical reaction in the presence of a catalyst metal.

Advantages of the Invention

According to the process for producing hydrogen or heavy hydrogens of the present invention, hydrogen or heavy hydrogens may be obtained from water or heavy water without the necessity of large-scale equipment and without problems of waste products and the like.

According to the process for producing a hydrogenated (protiated, deuterated or tritiated) organic compound and the process for hydrogenating (protiating, deuterating or tritiating) an organic compound of the invention, a hydrogenated (protiated, deuterated or tritiated) organic compound may be obtained conveniently without the use of expensive reagent and catalyst.

An organic compound that is deuterated or tritiated by the process for producing a deuterated or tritiated organic compound or the process for deuterating or tritiating an organic compound is useful as a labeled compound. The deuteration or tritiation of a drug containing a known organic compound may enhance the drug efficacy thereof.

According to the process for dehalogenating of the invention, an organic compound containing halogen may be dehalogenated conveniently without the use of expensive reagent and catalyst. The process may be utilized particularly for detoxifying an organic compound containing halogen that is toxic to humans, such as polychlorinated biphenyl (PCB).

EMBODIMENT FOR CARRYING OUT THE INVENTION

In the present invention including the invention relating to the process for producing hydrogen or heavy hydrogens (which may be hereinafter referred to as a first embodiment of the invention), the invention relating to the process for producing a hydrogenated (protiated, deuterated or tritiated) organic compound (which may be hereinafter referred to as a second embodiment of the invention), the invention relating to the process for hydrogenating (protiating, deuterating or tritiating) an organic compound (which may be hereinafter referred to as a third embodiment of the invention) and the process for dehalogenation (which may be hereinafter referred to as a fourth embodiment of the invention), it is necessary to perform mechanochemical reaction in the presence of a catalyst metal.

The term "heavy water" in the invention means water that is formed of $^2$H (D) or $^3$H (T), which is an isotope of hydrogen ($^1$H), and $^{17}$O or $^{18}$O, which is an isotope of oxygen ($^{16}$O) and combination thereof, and specific examples thereof include $D_2O$ and $T_2O$. The term "heavy hydrogen" herein means hydrogen that is formed of an isotope of hydrogen, and examples thereof include $D_2$ and $T_2$. The term "deuteration or tritiation" herein means that a part or the whole of hydrogen in ordinary hydrogenation is replaced by D or T.

The mechanochemical reaction that is performed in the invention is performed by enhancing the activity of the reactants with mechanical energy, such as impact and friction, and is performed generally with equipment capable of performing the mechanochemical reaction. Examples of the equipment include one having a reaction vessel and an agitation medium applying mechanical energy, and specific examples thereof include a ball mill, such as a planetary ball mill and a mixer mill, and a mixer, such as shaker. Among these, the use of a planetary ball mill is preferred in view of the agitation efficiency and the energy to be applied.

A planetary ball mill is equipment that has a function of uniformly mixing or finely pulverizing powder of metals or ceramics, and formed of a planetary ball mill reaction vessel and an atmosphere controlling section. Powder of metals or ceramics (i.e., a material to be pulverized) and balls as an agitation medium are placed in the ball mill reaction vessel, which is set in the equipment, and then the ball mill reaction vessel undergoes a revolution motion like a motion of a planet while undergoing a rotation motion in the atmosphere controlling section, thereby mixing and pulverizing the powder with high efficiency in a short period of time. Furthermore, the entire planetary ball mill is controlled in atmosphere, and thus powder that is denatured in the air may be mixed and pulverized.

Examples of the reaction vessel and the balls as an agitation medium used in the planetary ball mill include ones formed of such materials as stainless steel, agate, alumina, tungsten carbide, chrome steel, zirconia, silicon nitride and the like. Among these materials, stainless steel, which is an alloy of iron with chromium, nickel and the like, is preferred. The size of the vessel used in the planetary ball mill is not particularly limited and may be approximately 1 to 1,000 $cm^3$. The size of the balls is also not particularly limited and may be approximately from 2 to 20 mm in diameter. Particularly preferred specific examples of the planetary ball mill include Planetary Ball Mill Quartet P-7 (produced by Fritsch GmbH, Germany), Planetary Ball Mill Premium Line 7 (produced by Fritsch GmbH, Germany) and Planetary Ball Mill PM-100 (produced by Retsch GmbH, Germany).

For performing the mechanochemical reaction in the presence of the catalyst metal in the invention, it is sufficient to make the catalyst metal present in the mechanochemical reaction system in such an amount capable of exhibiting the catalytic action thereof, for example, an amount that is larger by 0.001% by mol or more with respect to water. Examples of the catalyst metal include a transition metal, such as palladium, iron, nickel and chromium, and oxides thereof, and preferred examples thereof include iron, iron(II) hydroxide, nickel, nickel(II) oxide, chromium, chromium(III) oxide and palladium. The catalyst metal may be used solely or as a combination of two or more kinds thereof. The catalyst metal may be added in the form of wire, foil or the like in the reaction vessel used for the mechanochemical reaction, may be contained in the agitation medium, such as balls and agitation bars, or may be plated on the agitation medium.

On practicing the process for producing hydrogen or heavy hydrogens as the first embodiment of the invention, water or heavy water may be subjected to mechanochemical reaction in the presence of a catalyst metal, preferably one kind or two or more kinds of a catalyst metal selected from iron, iron(II) hydroxide, chromium and chromium(III) oxide. Specifically, water or heavy water may be placed in the reaction vessel of the equipment capable of performing mechanochemical reaction, and mechanochemical reaction may be performed by operating the agitation medium in the presence of the catalyst metal, thereby forming hydrogen or heavy hydrogens. Finally, hydrogen or heavy hydrogens accumulated in the reaction vessel may be collected according to an ordinary method.

The first embodiment of the invention will be specifically described below for the case where a planetary ball mill is used. In a reaction vessel of a planetary ball mill, water or heavy water in an amount of from 0.1 to 20% by mass (which may be hereinafter referred simply to "%") based on the capacity of the vessel is placed, to which approximately from 1 to 100 pieces of an agitation medium (balls) and, depending on necessity, approximately from 0.01 to 100% by mol of a catalyst metal, with respect to an organic compound, in addition to the catalyst metal contained in the reaction vessel and the agitation medium are added, and they are agitated by operating the planetary ball mill for approximately from 0.1 to 12 hours, and preferably approximately from 0.5 to 6 hours, at approximately from 400 to 1,200 rpm, and preferably approximately from 800 to 1,100 rpm. On agitating, the rotation direction is preferably reversed appropriately depending on necessity, and in the case where the rotation is continuously performed, a down period is preferably provided. In the first embodiment of the invention, the conversion efficiency of from water or heavy water to hydrogen or heavy hydrogens is approximately from 20 to 100% while depending on the equipment, the reaction conditions and the like employed.

Hydrogen or heavy hydrogens that are obtained by the first embodiment of the invention may be utilized for electric power generation with a fuel cell or by cold nuclear fusion with heavy hydrogens.

On practicing the process for producing a hydrogenated (protiated, deuterated or tritiated) organic compound as the second embodiment of the invention, an organic compound and water or heavy water may be subjected to mechanochemical reaction in the presence of a catalyst metal, preferably one kind or two or more kinds of a catalyst metal selected from nickel, nickel (II) oxide, chromium, chromium (III) oxide and palladium. Specifically, an organic compound and water or heavy water may be placed in the reaction vessel of the equipment capable of performing mechanochemical reaction, and mechanochemical reaction may be performed by operating the agitation medium in the presence of the catalyst metal, thereby hydrogenating (protiating, deuterating or tritiating) the organic compound. The hydrogenation (protiation, deuteration or tritiation) of the organic compound may be confirmed by a known method, such as $^1$H-NMR and GC/MS.

The organic compound used in the second embodiment of the invention is not particularly limited as far as it is an organic compound that may be hydrogenated (protiated, deuterated or tritiated), and examples thereof include an organic compound that has in the skeleton thereof an unsaturated bond, such as a double bond and a triple bond, a substituent having a large oxidation degree, such as an aldehyde group, a ketone group, a nitro group and an azido group, a halogen atom, or the like.

In the second embodiment of the invention, the extent of hydrogenation (protiation, deuteration or tritiation) of the organic compound may be controlled by the amount of water or heavy water added with the organic compound since hydrogen or heavy hydrogens are introduced thereby. In the case where the extent of hydrogenation (protiation, deuteration or tritiation) is to be increased, the amount of the water or heavy water may be large, and in the case where the extent of hydrogenation (protiation, deuteration or tritiation) may be low, the amount of the water or heavy water may be small. The amount of water or heavy water is largely influenced by the possibility of hydrogenation (protiation, deuteration or tritiation) of the organic compound, and thus may be determined experimentally on practicing. In the second embodiment of the invention, the extent of hydrogenation (protiation, deuteration or tritiation) of the organic compound may also be controlled by the mechanical energy, such as impact and friction, on the mechanochemical reaction. In the case where the extent of hydrogenation (protiation, deuteration or tritiation) is to be increased, the size of the balls may be increased, the number of balls may be increased, or the rotation speed may be increased, and in the case where the extent of hydrogenation (protiation, deuteration or tritiation) may be low, the size of the balls may be small, the number of balls may be small, or the rotation speed may be small.

On practicing the second embodiment of the invention according to the aforementioned manner, water or heavy water in the reaction vessel is converted to hydrogen or heavy hydrogens, with which the organic compound is hydrogenated (protiated, deuterated or tritiated). In the second embodiment of the invention, the conversion efficiency of from the organic compound to the hydrogenated (protiated, deuterated or tritiated) organic compound is approximately from 70 to 100% while depending on the equipment, the reaction conditions and the like employed.

According to the second embodiment of the invention, an unsaturated bond (such as a double bond and a triple bond) in a skeleton of an organic compound may be converted to a saturated bond, and it is also possible that a substituent having a large oxidation degree (such as an aldehyde group, a ketone group and a nitro group) may be converted to a substituent having a small oxidation degree (such as a hydroxyalkyl group, a hydroxyl group and an amino group), and a halogen atom in a halogenated compound may be removed to form a dehalogenated compound.

Specifically, compounds having the following skeletons may be converted to corresponding reduced compounds through hydrogenation (protiation, deuteration or tritiation). Examples of the compounds capable of being hydrogenated (protiated, deuterated or tritiated) are shown below, but the compounds capable of being hydrogenated (protiated, deuterated or tritiated) by the second embodiment of the invention are not limited thereto. In the following compounds, a methyl group is described as a representative example of an alkyl group (a functionalized aliphatic chain), and benzene or phenyl is described as a representative example of an aryl group (a functionalized aromatic ring (including benzene, furan, pyrrole, thiophene and the like).

<Triple Bond-containing Compound>
Terminal alkyne compound:
methyl acetylene and ethynylbenzene
Disubstituted alkyne compound:
diphenylacetylene, dimethylacetylene and methylphenylacetylene <Double Bond-containing Compound>
Monosubstituted alkene compound:
phenylethylene and methylethylene
Disubstituted alkene compound:
(E)-1,2-diphenylethylene, (Z)-1,2-diphenylethylene, (E)-1,2-dimethylethylene, (Z)-1,2-dimethylethylene, 1,1-diphenylethylene, 1,1-dimethylethylene, 1-methyl-1-phenylethylene, (E)-1-methyl-2-phenylethylene and (Z)-1-methyl-2-phenylethylene
Trisubstituted alkene compound:
1,1,2-triphenylethylene, 1,1,2-trimethylethylene, 1,1-diphenyl-2-methylethylene and 1-phenyl-1,2-dimethylethylene
Tetrasubstituted alkene compound:
1,1,2,2-tetraphenylethylene, 1,1,2,2-tetramethylethylene, 1,1,2-triphenyl-2-methylethylene, 1,1-diphenyl-2,2-dimethylethylene, 1-phenyl-1,2,2-trimethylethylene, (E)-1,2-diphenyl-1,2-dimethylethylene and (Z)-1,2-diphenyl-1,2-dimethylethylene
Aromatic ring:
benzene, biphenyl, pyridine, furan, pyrrole, thiophene, naphthalene, quinoline, anthracene, imidazole, indole, benzofuran and oxazole <Carbonyl Group-containing Compound[*]>
Aldehyde compound:
methylaldehyde and phenylaldehyde
Ketone compound:
dimethyl ketone, diphenyl ketone and methyl phenyl ketone
Imine compound:
N-methyl-methylimine, N-phenyl-methylimine, N-methyl-dimethylimine, N-methyl-diphenylimine, N-methyl-methylphenylimine, N-phenyl-dimethylimine, N-phenyl-diphenylimine and N-phenyl-methylphenylimine Oxime:
N-hydroxy-methylimine, N-hydroxy-dimethylimine, N-hydroxy-diphenylimine and N-hydroxy-methylphenylimine Note: (*) Compounds where an oxygen atom of a carbonyl group is substituted by other atom or group are included.

<Nitro Group-containing Compound>
Nitro compound:
nitromethane and nitrobenzene <Azide Group-containing Compound>
Azide compound:
methyl azide and phenyl azide <Halogen-containing Compound>
Fluorinated compound:
methyl fluoride and fluorobenzene
Chlorinated compound:
methyl chloride and chlorobenzene
Brominated compound:
methyl bromide and bromobenzene
Iodinated compound:
methyl iodide and iodobenzene <Benzyl Ether Group-containing Compound>
Benzyl ether compound:
phenyl methyl oxy methane and phenyl methyl oxy benzene Particularly preferred specific examples of the compound to be hydrogenated (protiated, deuterated or tritiated) and the corresponding reduced compounds thereof in the second embodiment of the invention are shown below.

| Compound to be hydrogenated (protiated, deuterated or tritiated) | Reduced compound |
| --- | --- |
| ethynylbenzene | ethylbenzene |
| diphenylacetylene | 1,2-diphenylethane |
| phenylethylene | ethylbenzene |
| (E)-1,2-diphenylethylene | 1,2-diphenylethane |
| (Z)-1,2-diphenylethylene | 1,2-diphenylethane |
| 1,1-diphenylethylene | 1,1-diphenylethane |
| phenylaldehyde | benzyl alcohol |
| methyl phenyl ketone | 1-phenylethanol |
| nitrobenzene | aminobenzene |
| phenyl azide | aminobenzene |
| chlorobenzene | benzene |
| phenyl methyl oxy benzene | phenol |

The conditions where the second embodiment of the invention is performed with a planetary ball mill may be the same as those in the first embodiment of the invention except that approximately from 0.1 to 20% of water or heavy water based on the capacity of the vessel and approximately from 0.01 to 20% of the organic compound based on the capacity of the vessel are placed in the reaction vessel of the planetary ball mill. In the second embodiment of the invention, the conversion efficiency of from the organic compound to the hydrogenated (protiated, deuterated or tritiated) organic compound is approximately from 70 to 100% while depending on the equipment, the reaction conditions and the like employed.

The organic compound that has been deuterated or tritiated in the second embodiment of the invention is useful as a labeled compound used for structural analysis and analysis of mechanisms. Furthermore, the deuteration or tritiation of a drug containing a known organic compound through the second embodiment of the invention may enhance the drug efficacy thereof.

The process for hydrogenating (protiating, deuterating or tritiating) an organic compound as the third embodiment of the invention may be practiced in the same manner as in the second embodiment of the invention.

The process for dehalogenation as the fourth embodiment of the invention may also be practiced in the same manner as in the second embodiment of the invention. Particularly, the process may dehalogenate an organic compound containing halogen that is toxic to humans, such as polychlorinated biphenyl (PCB), and thus may be utilized for detoxifying the organic compound.

EXAMPLE

The present invention will be described in more detail with reference to examples below, but the invention is not limited to the examples. The planetary ball mills used in the examples have the following features. In the examples, the structures and the like of the products are confirmed by GC/MS and $^1$H-NMR even though not mentioned.

Examples 1 to 15, 18 to 20, and 22 to 24

Equipment used:
Planetary Ball Mill Quartet P-7, produced by Fritsch GmbH, Germany
Rotation/revolution ratio: 1/−2
Balls: diameter: 5 to 6 mm, material: stainless steel
Vessel: capacity: 12 mL, material: stainless steel
Composition of stainless steel:
Fe: (approx.) 67 to 70%
C: 0.12%
Si: 1%
Mn: 2%
P: 0.06%
S: 0.15 to 0.35%
Cr: 17 to 19%
Ni: 8 to 10%

Example 16

Equipment used:
Planetary Ball Mill PM-100, produced by Retsch GmbH, Germany
Rotation/revolution ratio: 1/−2
Balls: diameter: 10 mm, material: stainless steel
Vessel: capacity: 250 mL, material: stainless steel
Composition of stainless steel:
Fe: 82.925%
Cr: 14.5%
Mn: 1%
Si: 1%
C: 0.5%
P: 0.045%
S: 0.03%

Examples 17 and 21

Equipment used:
Planetary Ball Mill Premium Line 7, produced by Fritsch GmbH, Germany
Rotation/revolution ratio: 1/−2
Balls: diameter: 5 to 6 mm, material: stainless steel
Vessel: capacity: 20 mL (Example 17) or 80 mL (Example 21), material: stainless steel
Composition of stainless steel:
Fe: (approx.) 67 to 70%
C: 0.12%
Si: 1%

Mn: 2%
P: 0.06%
S: 0.15 to 0.35%
Cr: 17 to 19%
Ni: 8 to 10%

Example 1

Decomposition of Water to Hydrogen

270 μL (15 mmol) of distilled water (Wako 046-16971) and stainless steel balls (50 pieces) were placed in the vessel of the planetary ball mill, which was then closed, and agitated by operating the planetary ball mill for 6 hours at 800 rpm (reversed every 30 minutes). After completing the agitation, the vessel was opened, and the gas in the vessel was ignited and thus was combusted. The combustion phenomenon confirmed formation of hydrogen gas as a combustible gas. The reaction is expressed by the following scheme.

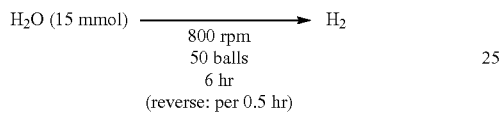

Example 2

Hydrogenation Reaction of diphenylacetylene (1) Synthesis of 1,2-diphenylethane (2)

89.1 mg (0.50 mmol) of diphenylacetylene (1), 270 μL (15 mmol) of distilled water and stainless steel balls (50 pieces) were placed in the vessel of the planetary ball mill, which was then closed, and agitated by operating the planetary ball mill for 12 hours at 800 rpm (reversed every 30 minutes). After the lapse of 12 hours, 10 mL of ethyl acetate was added to the vessel of the ball mill to provide a solution containing the reaction mixture, which was then filtered with celite. The operation was repeated 5 times to provide a filtrate, which was then concentrated, thereby providing 89.4 mg (0.49 mmol) of 1,2-diphenylethane (2). The yield was 98%.

(2) Synthesis of 1,2-diphenylethane (2), 1-cyclohexyl-2-phenylethane (3) and 1,2-dicyclohexylethane (4)

89.1 mg (0.50 mmol) of diphenylacetylene (1), 900 μL (50 mmol) of distilled water and stainless steel balls (50 pieces) were placed in the vessel of the planetary ball mill, which was then closed, and agitated by operating the planetary ball mill for 12 hours at 800 rpm (reversed every 30 minutes). After the lapse of 12 hours, 10 mL of ethyl acetate was added to the vessel of the ball mill to provide a solution containing the reaction mixture, which was then filtered with celite. The operation was repeated 5 times to provide a filtrate, which was then concentrated, thereby providing reaction products. Analysis of the products with GC/MS and $^1$H-NMR revealed that the products were a mixture of 1,2-diphenylethane (2), 1-cyclohexyl-2-phenylethane (3) and 1,2-dicyclohexylethane (4). The reaction is expressed by the following scheme.

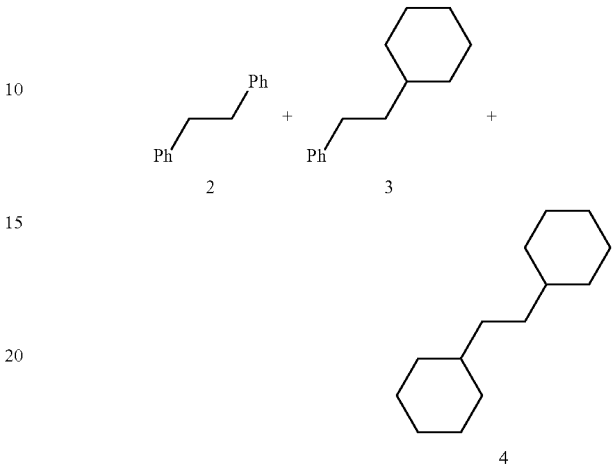

It is understood from the results that the extent of hydrogenation of an organic compound can be controlled by the amount of water added to the organic compound.

Example 3

Synthesis of 4-aminobenzophenone by hydrogenation reaction of 4-azidobenzophenone 111.6 mg (0.50 mmol) of 4-azidobenzophenone (5), 270 μL (15 mmol) of distilled water and stainless steel balls (50 pieces) were placed in the vessel of the planetary ball mill, which was then closed, and agitated by operating the planetary ball mill for 12 hours at 800 rpm (reversed every 30 minutes). After the lapse of 12 hours, 10 mL of ethyl acetate was added to the vessel of the ball mill to provide a solution containing the reaction product, which was then filtered with celite. The operation was repeated 5 times to provide a filtrate, which was then concentrated, thereby providing 87.7 mg (0.45 mmol) of 4-aminobenzophenone (6). The yield was 89%. The reaction is expressed by the following scheme.

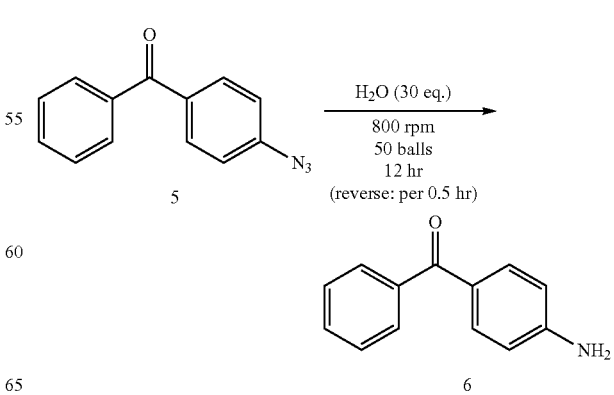

Example 4

Synthesis of 3-benzyloxy-4-methoxybenzyl alcohol and 3-hydroxy-4-methoxybenzyl alcohol by hydrogenation reaction of 3-benzyloxy-4-methoxybenzaldehyde 121.1 mg (0.50 mmol) of 3-benzyloxy-4-methoxybenzaldehyde (7), 270 μL (15 mmol) of distilled water and stainless steel balls (50 pieces) were placed in the vessel of the planetary ball mill, which was then closed, and agitated by operating the planetary ball mill for 12 hours at 800 rpm (reversed every 30 minutes). After the lapse of 12 hours, 10 mL of ethyl acetate was added to the vessel of the ball mill to provide a solution containing the reaction mixture, which was then filtered with celite. The operation was repeated 5 times to provide a filtrate, which was then concentrated, thereby providing 74.0 mg (0.31 mmol) of 3-benzyloxy-4-methoxybenzyl alcohol (8) and 6.9 mg (0.05 mmol) of 3-hydroxy-4-methoxybenzyl alcohol (9). The yields were 61% and 9%, respectively. The reaction is expressed by the following scheme. 23.7 mg (0.10 mmol) of unreacted 3-benzyloxy-4-methoxybenzaldehyde (7) was recovered.

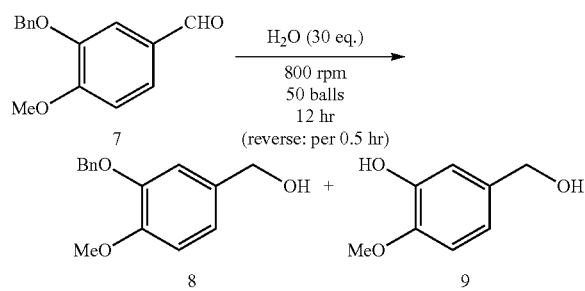

Example 5

Synthesis of 4-amino-1-methoxybenzene by hydrogenation reaction of 1-methoxy-4-nitrobenzene 76.6 mg (0.50 mmol) of 1-methoxy-4-nitrobenzene (10), 270 μL (15 mmol) of distilled water and stainless steel balls (50 pieces) were placed in the vessel of the planetary ball mill, which was then closed, and agitated by operating the planetary ball mill for 12 hours at 800 rpm (reversed every 30 minutes). After the lapse of 12 hours, 10 mL of ethyl acetate was added to the vessel of the ball mill to provide a solution containing the reaction mixture, which was then filtered with celite. The operation was repeated 5 times to provide a filtrate, which was then concentrated, thereby providing 48.2 mg (0.39 mmol) of 4-amino-1-methoxybenzene (11). The yield was 78%. The reaction is expressed by the following scheme.

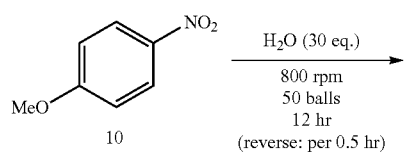

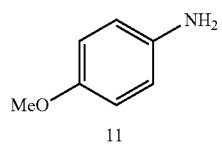

Example 6

Synthesis of 4-ethyl-1-methoxybenzene by hydrogenation reaction of 4-ethynyl-1-methoxybenzene 64.8 μL (0.50 mmol) of 4-ethynyl-1-methoxybenzene (12), 270 μL (15 mmol) of distilled water and stainless steel balls (50 pieces) were placed in the vessel of the planetary ball mill, which was then closed, and agitated by operating the planetary ball mill for 12 hours at 800 rpm (reversed every 30 minutes). After the lapse of 12 hours, 10 mL of ethyl acetate was added to the vessel of the ball mill to provide a solution containing the reaction mixture, which was then filtered with celite. The operation was repeated 5 times to provide a filtrate, which was then concentrated, thereby providing 47.0 mg (0.35 mmol) of 4-ethyl-1-methoxybenzene (13). The yield was 69%. The reaction is expressed by the following scheme.

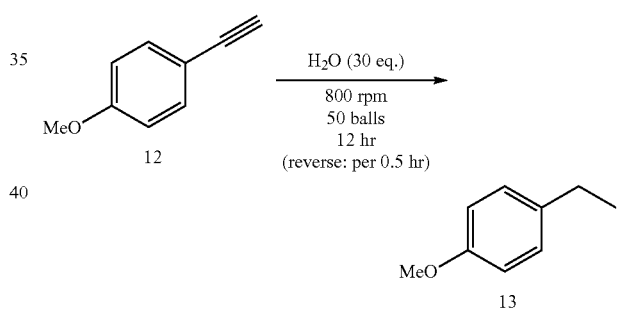

Example 7

Synthesis of methoxybenzene by hydrogenation reaction of 4-chloro-1-methoxybenzene 61.3 μL (0.50 mmol) of 4-chloro-1-methoxybenzene (14), 270 μL (15 mmol) of distilled water and stainless steel balls (50 pieces) were placed in the vessel of the planetary ball mill, which was then closed, and agitated by operating the planetary ball mill for 12 hours at 800 rpm (reversed every 30 minutes). After the lapse of 12 hours, 10 mL of ethyl acetate was added to the vessel of the planetary ball mill to provide a solution containing the reaction mixture, which was then filtered with celite. The operation was repeated 5 times to provide a filtrate, which was then concentrated, thereby providing methoxybenzene (15). The conversion efficiency was 100%. The reaction is expressed by the following scheme.

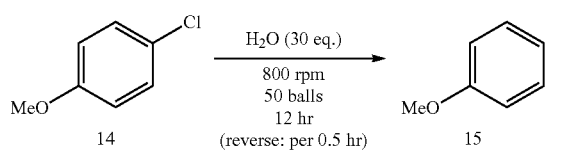 [SMILES: COc1ccc(Cl)cc1 ; COc1ccccc1]

Example 8

Deuteration Reaction of diphenylacetylene with Heavy Water (D₂O)

89.1 mg (0.50 mmol) of diphenylacetylene (1), 272 μL (15 mmol) of heavy water (Cambridge Isotope Laboratories, Inc., Cat. No. 15, 188-2) and stainless steel balls (50 pieces) were placed in the vessel of the planetary ball mill, which was then closed, and agitated by operating the planetary ball mill for 12 hours at 800 rpm (reversed every 30 minutes). After the lapse of 12 hours, 10 mL of ethyl acetate was added to the vessel of the planetary ball mill to provide a solution containing the reaction mixture, which was then filtered with celite. The operation was repeated 5 times to provide a filtrate, which was then concentrated, thereby providing 85.9 mg (0.46 mmol) of 1,2-diphenyl-1,1,2,2-tetradeuteroethane (16). The yield was 93%. The structure of the product was confirmed with ¹H-NMR and GC/MS. The reaction is expressed by the following scheme.

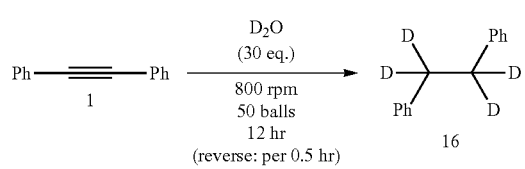

Example 9

Synthesis of 1-aminonaphthalene by hydrogenation reaction of 1-nitronaphthalene 86.6 mg (0.50 mmol) of 1-nitronaphthalene (17), 270 μL (15 mmol) of distilled water and stainless steel balls (50 pieces) were placed in the vessel of the planetary ball mill, which was then closed, and agitated by operating the planetary ball mill for 12 hours at 800 rpm (reversed every 30 minutes). After the lapse of 12 hours, 10 mL of ethyl acetate was added to the vessel of the planetary ball mill to provide a solution containing the reaction mixture, which was then filtered with celite. The operation was repeated 5 times to provide a filtrate, which was then concentrated, thereby providing 44.3 mg (0.31 mmol) of 1-aminonaphthalene (18). The yield was 62%. The conversion yield was 100%, but the isolated yield was lowered since the product was partially distilled off under reduced pressure. The reaction is expressed by the following scheme.

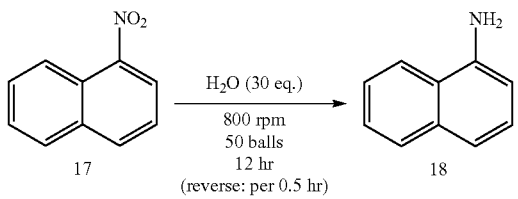 [SMILES: O=[N+]([O-])c1cccc2ccccc12 ; Nc1cccc2ccccc12]

Example 10

Synthesis of naphthalene by hydrogenation Reaction of 1-chloronaphthalene 68.4 μL (0.50 mmol) of 1-chloronaphthalene (19), 270 μL (15 mmol) of distilled water and stainless steel balls (50 pieces) were placed in the vessel of the planetary ball mill, which was then closed, and agitated by operating the planetary ball mill for 12 hours at 800 rpm (reversed every 30 minutes). After the lapse of 12 hours, 10 mL of ethyl acetate was added to the vessel of the planetary ball mill to provide a solution containing the reaction mixture, which was then filtered with celite. The operation was repeated 5 times to provide a filtrate, which was then concentrated, thereby providing 10.4 mg (0.08 mmol) of naphthalene (20). The yield was 16%. The conversion yield was 100%, but the isolated yield was lowered since the product was partially distilled off under reduced pressure. The reaction is expressed by the following scheme.

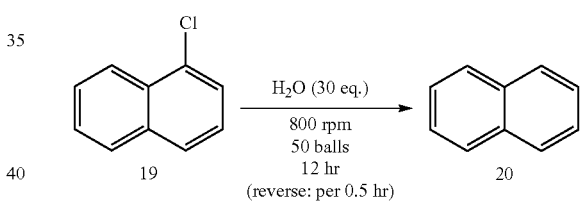

Example 11

Hydrogenation Reaction Inhibiting Effect with tetracyanoquinodimethane (TCNQ)

89.1 mg (0.50 mmol) of diphenylacetylene (1), 270 μL (15 mmol) of distilled water, 10.1 mg (0.05 mmol) of tetracyanoquinodimethane (TCNQ) and stainless steel balls (50 pieces) were placed in the vessel of the planetary ball mill, which was then closed, and agitated by operating the planetary ball mill for 12 hours at 800 rpm (reversed every 30 minutes). In the system, completely no reaction proceeded even when the agitation was performed continuously for 12 hours. It is expected that this is because the reaction proceeds through radicals. The reaction is expressed by the following scheme.

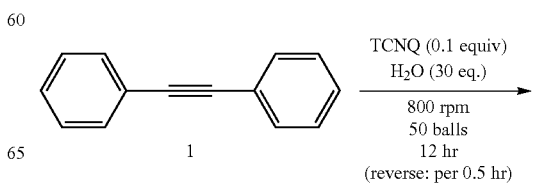

No reaction

Example 12

Synthesis of 4-aminobenzophenone by hydrogenation reaction of 4-nitrobenzophenone 91.1 mg (0.50 mmol) of 4-nitrobenzophenone (21), 270 μL (15 mmol) of distilled water and stainless steel balls (50 pieces) were placed in the vessel of the planetary ball mill, which was then closed, and agitated by operating the planetary ball mill for 12 hours at 800 rpm (reversed every 30 minutes). After the lapse of 12 hours, 10 mL of ethyl acetate was added to the vessel of the planetary ball mill to provide a solution containing the reaction mixture, which was then filtered with celite. The operation was repeated 5 times to provide a filtrate, which was then concentrated, thereby providing 4-aminobenzophenone (22) and 4-aminobenzhydrol (23) at a ratio of 83/17 confirmed by $^1$H-NMR. The reaction is expressed by the following scheme.

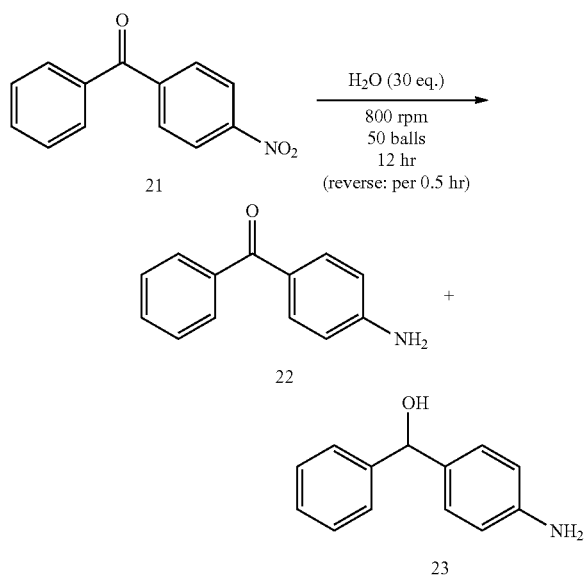

Example 13

Synthesis of 4-benzyloxybenzene by hydrogenation Reaction of 4-benzyloxybromobenzene 131.6 mg (0.50 mmol) of 4-benzyloxybromobenzene (24), 270 μL (15 mmol) of distilled water and stainless steel balls (50 pieces) were placed in the vessel of the planetary ball mill, which was then closed, and agitated by operating the planetary ball mill for 12 hours at 800 rpm (reversed every 30 minutes). After the lapse of 12 hours, 10 mL of ethyl acetate was added to the vessel of the planetary ball mill to provide a solution containing the reaction mixture, which was then filtered with celite. The operation was repeated 5 times to provide a filtrate, which was then concentrated, thereby providing 4-benzyloxybromobenzene (24) and 4-benzyloxybenzene (25) at a ratio of 9/91 confirmed by $^1$H-NMR. The reaction is expressed by the following scheme.

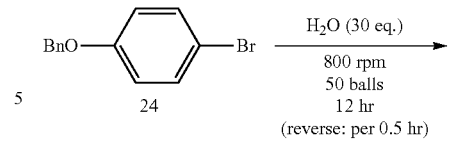

Example 14

Hydrogenation Reaction with Addition of Palladium Foil 89.1 mg (0.50 mmol) of diphenylacetylene (1), 270 μL (15 mmol) of distilled water, stainless steel balls (50 pieces) and palladium foil (produced by Sigma-Aldrich Corporation) in amounts shown in the following table were placed in the vessel of the planetary ball mill, which was then closed, and agitated by operating the planetary ball mill for periods of time shown in the following table at 800 rpm (reversed every 30 minutes). After the agitation, 10 mL of ethyl acetate was added to the vessel of the ball mill to provide a solution containing the reaction mixture, which was then filtered with celite. The operation was repeated 5 times to provide a filtrate, which was then concentrated, thereby providing reaction products. Analysis of the products with $^1$H-NMR revealed that the products were a mixture of cis-1,2-diphenylethylene (26), trans-1,2-diphenylethylene (27) and 1,2-diphenylethane (2). The formation ratios of these compounds were as shown in the following table. In the system, the addition of palladium foil shortened the time required for the formation and improved the formation ratios. The reaction is expressed by the following scheme.

TABLE 1

| Amount of palladium foil | Time (hr) | Formation ratio (1)/(26)/(27)/(2) |
|---|---|---|
| 2.7 mg (5 mol %) | 3 | 0/0/0/100 |
| 1.6 mg (3 mol %) | 1 | 69/26/1/3 |
|  | 3 | 0/16/8/76 |
| none | 1 | 92/5/1/2 |
|  | 3 | 0/36/8/56 |

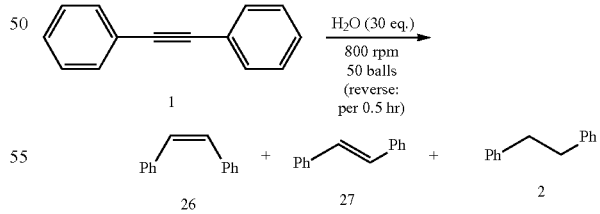

Example 15

Dechlorination Reaction with Addition of Palladium Foil 148.5 mg (0.50 mmol) of 4-chlorododecyloxybenzene (28), 270 μL (15 mmol) of distilled water, 1.9 mg (3.6% by mol) of palladium foil and stainless steel balls (50 pieces)

were placed in the vessel of the planetary ball mill, which was then closed, and agitated by operating the planetary ball mill for 12 hours at 800 rpm (reversed every 30 minutes). After the lapse of 12 hours, 10 mL of ethyl acetate was added to the vessel of the ball mill to provide a solution containing the reaction mixture, which was then filtered with celite. The operation was repeated 5 times to provide a filtrate, which was then concentrated, thereby providing 58.7 mg (0.22 mmol) of dodecyloxybenzene (29) at a yield of 45%. The conversion efficiency was 100%. The reaction is expressed by the following scheme.

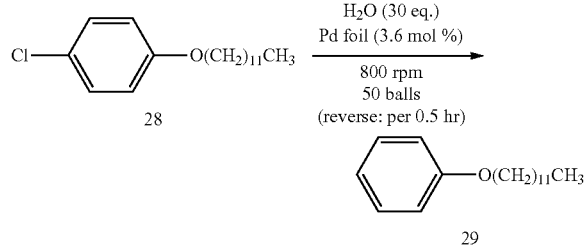

Example 16

Hydrogenation Reaction of diphenylacetylene 1.34 g (7.5 mmol) of diphenylacetylene (1), 4.01 mL (225 mmol) of distilled water and stainless steel balls (25 pieces) were placed in the vessel of the planetary ball mill, which was then closed, and agitated by operating the planetary ball mill for 6 hours at 650 rpm (reversed every 30 minutes). After the lapse of 6 hours, 200 mL of ethyl acetate was added to the vessel of the ball mill to provide a solution containing the reaction mixture, which was then filtered with celite. The filtrate was concentrated, thereby providing reaction products. The confirmation by $^1$H-NMR thereof revealed that a mixture of cis-1,2-diphenylethylene (26), trans-1,2-diphenylethylene (27) and 1,2-diphenylethane (2) was obtained at a mixing ratio of 92/0/8. The yield was 92%. The reaction is expressed by the following scheme.

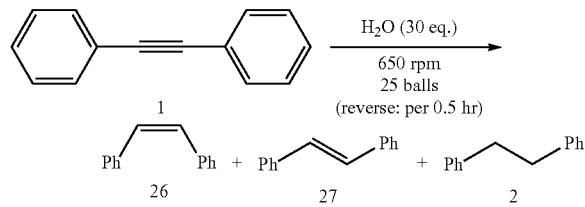

Example 17

Investigation on Hydrogen Formation Condition

270 μL (15 mmol) of distilled water (Wako 046-16971) and stainless steel balls (50 pieces) were placed in the vessel of the planetary ball mill, which was then closed, and agitated by operating the planetary ball mill for 1 hour at from 400 to 1,000 rpm (reversed every 30 minutes) or for 0.3 hour at 1,100 rpm (without reverse). After completing the agitation, the composition of the gas in the vessel was analyzed with GC/TCD (GC-2014, produced by Shimadzu Corporation). The results are shown in Table 2 below.

TABLE 2

| Rotation number (rpm) | Collected amount (mL) | Time (h) | Internal gas (%) | | | | |
|---|---|---|---|---|---|---|---|
| | | | H$_2$ | N$_2$ | O$_2$ | CO$_2$ | CO |
| theoretical values* | 417 | — | 81 | 15 | 4 | <0.1 | <0.1 |
| 400 | 80 | 1 | 13 | 76 | 2.1 | 0.25 | <0.1 |
| 600 | 300 | 1 | 39 | 39 | 3.6 | 0.15 | <0.1 |
| 800 | 400 | 1 | 55 | 21 | 1.4 | 0.16 | <0.1 |
| 900 | 400 | 1 | 56 | 26 | 2.1 | 0.18 | <0.1 |
| 1,000 | 400 | 1 | 49 | 22 | 1.2 | 0.23 | <0.1 |
| 1,100 | 350 | 0.3 | 43 | 30 | 1.9 | 0.21 | <0.1 |

Note:
*Theoretical values on complete decomposition of water

It was found from the results that in decomposition of water with a ball mill, only hydrogen was formed, but oxygen was not increased. Accordingly, the process of the present invention is an extremely safe hydrogen formation method with a slight amount of oxygen formed. In the process of the invention, it is considered that high-purity hydrogen may be formed and collected by vacuumizing the interior of the ball mill.

Example 18

Synthesis of dodecane by hydrogenation Reaction of 6-dodecyne 83.2 mg (0.50 mmol) of 6-dodecyne (30), 270 μL (15 mmol) of distilled water and stainless steel balls (50 pieces) were placed in the vessel of the planetary ball mill, which was then closed, and agitated by operating the planetary ball mill for 6 hours at 800 rpm (reversed every 30 minutes). After the lapse of 6 hours, 10 mL of ethyl acetate was added to the vessel of the ball mill to provide a solution containing the reaction mixture, which was then filtered with celite. The operation was repeated 5 times to provide a filtrate, which was then concentrated, thereby providing 51.1 mg (0.30 mmol) of dodecane (31). The yield was 60%. The reaction is expressed by the following scheme.

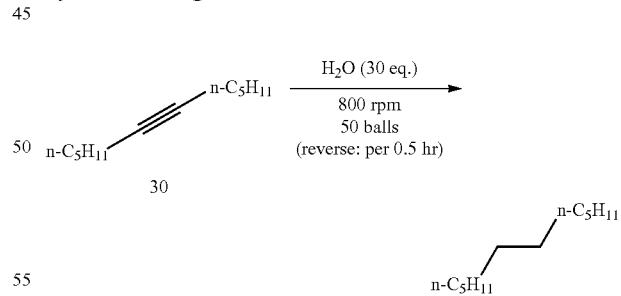

Example 19

Synthesis of 1-phenylethanol by hydrogenation Reaction of 1-phenylethanone 60.1 mg (0.50 mmol) of 1-phenylethanone (32), 270 μL (15 mmol) of distilled water and stainless steel balls (50 pieces) were placed in the vessel of the planetary ball mill, which was then closed, and agitated by operating the planetary ball mill for 6 hours at 800 rpm (reversed every 30 minutes). After the lapse of 6 hours, 10 mL of ethyl acetate was added to the vessel of the ball mill to provide a solution containing the reaction mixture, which was then filtered with celite. The operation was repeated 5 times to provide a filtrate, which was then concentrated, thereby providing 42.8 mg (0.35 mmol) of 1-phenylethanol (33). The yield was 70%. The reaction is expressed by the following scheme.

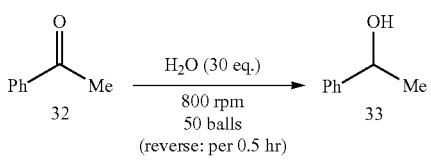 [SMILES: CC(=O)c1ccccc1 ; CC(O)c1ccccc1]

Example 20

Synthesis of 3-phenyl-1-propanol by hydrogenation Reaction of 3-phenyl-2-propen-1-ol 67.1 mg (0.50 mmol) of 3-phenyl-2-propen-1-ol (34), 270 µL (15 mmol) of distilled water and stainless steel balls (50 pieces) were placed in the vessel of the planetary ball mill, which was then closed, and agitated by operating the planetary ball mill for 6 hours at 800 rpm (reversed every 30 minutes). After the lapse of 6 hours, 10 mL of ethyl acetate was added to the vessel of the ball mill to provide a solution containing the reaction mixture, which was then filtered with celite. The operation was repeated 5 times to provide a filtrate, which was then concentrated, thereby providing 64.7 mg (0.475 mmol) of 3-phenyl-1-propanol (35). The yield was 95%. The reaction is expressed by the following scheme.

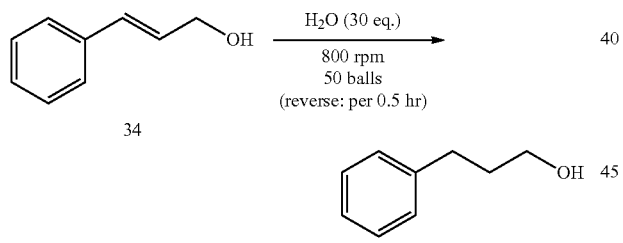

Example 21

Synthesis of 1,3-dimethoxybenzene by hydrogenation Reaction of 1-chloro-3,5-dimethoxybenzene 86.3 mg (0.50 mmol) of 1-chloro-3,5-dimethoxybenzene (36), 45 µL (2.5 mmol) of distilled water and stainless steel balls (50 pieces) were placed in the vessel of the planetary ball mill, which was then closed, and agitated by operating the planetary ball mill for 30 minutes at 1,100 rpm. After the lapse of 30 minutes, 10 mL of ethyl acetate was added to the vessel of the ball mill to provide a solution containing the reaction mixture, which was then filtered with celite. The operation was repeated 5 times to provide a filtrate, which was then concentrated, thereby providing 36.6 mg (0.265 mmol) of 1,3-dimethoxybenzene (37). The yield was 53%. The reaction is expressed by the following scheme.

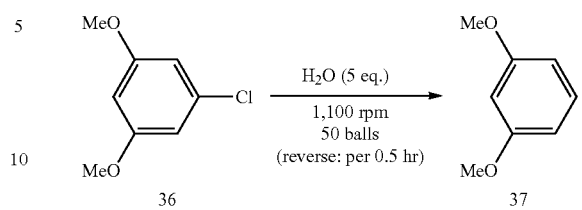

Example 22

Synthesis of 3-phenyl-2,3-dideutero-1-propanol by Deuteration of 3-phenyl-2-propen-1-ol 67.1 mg (0.50 mmol) of 3-phenyl-2-propen-1-ol (34), 272 µL (15 mmol) of heavy water and stainless steel balls (50 pieces) were placed in the vessel of the planetary ball mill, which was then closed, and agitated by operating the planetary ball mill for 6 hours at 800 rpm (reversed every 30 minutes). After the lapse of 6 hours, 10 mL of ethyl acetate was added to the vessel of the ball mill to provide a solution containing the reaction mixture, which was then filtered with celite. The operation was repeated 5 times to provide a filtrate, which was then concentrated, thereby providing 60.1 mg (0.435 mmol) of 3-phenyl-2,3-dideutero-1-propanol (38). The deuteration degree at the 2- and 3-positions was 50%, and the yield was 87%. The reaction is expressed by the following scheme.

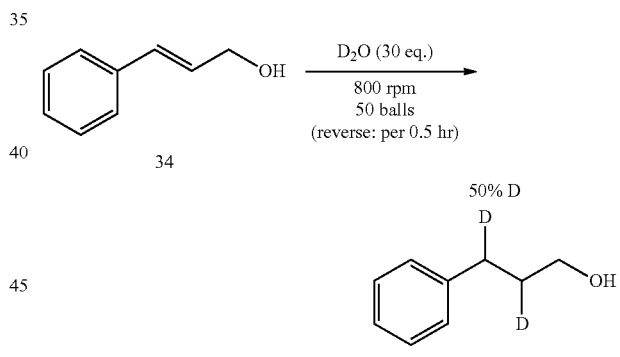

Example 23

Deuteration Reaction of benzyl 4-bromophenyl ketone (39)

(1) Synthesis of 1-(4-bromophenyl)-2,2-dideutero-2-phenylethane (40)

137.6 mg (0.50 mmol) of benzyl 4-bromophenyl ketone (39), 272 µL (15 mmol) of heavy water and stainless steel balls (50 pieces) were placed in the vessel of the planetary ball mill, which was then closed, and agitated by operating the planetary ball mill for 6 hours at 650 rpm (reversed every 30 minutes). After the lapse of 6 hours, 10 mL of ethyl acetate was added to the vessel of the ball mill to provide a solution containing the reaction mixture, which was then filtered with celite. The operation was repeated 5 times to provide a filtrate, which was then concentrated, thereby providing 128.9 mg (0.465 mmol) of 1-(4-bromophenyl)-2,2-dideutero-2-phenylethane (40). The deuteration degree at the 2-position was 77%, and the yield was 93%. The reaction is expressed by the following scheme.

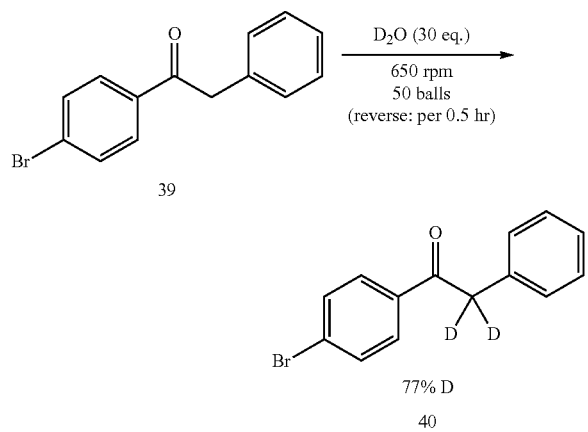

(2) Synthesis of 1-(4-bromophenyl)-2,2-dideutero-2-phenylethane (40) and 2,2-dideutero-1,2-diphenylethanone (41)

137.6 mg (0.50 mmol) of benzyl 4-bromophenyl ketone (39), 272 μL (15 mmol) of heavy water and stainless steel balls (50 pieces) were placed in the vessel of the planetary ball mill, which was then closed, and agitated by operating the planetary ball mill for 6 hours at 800 rpm (reversed every 30 minutes). After the lapse of 6 hours, 10 mL of ethyl acetate was added to the vessel of the ball mill to provide a solution containing the reaction mixture, which was then filtered with celite. The operation was repeated 5 times to provide a filtrate, which was then concentrated, thereby providing 124.7 mg (0.45 mmol) of 1-(4-bromophenyl)-2,2-dideutero-2-phenylethane (40) and 5.9 mg (0.03 mmol) of 2,2-dideutero-1,2-diphenylethanone (41). The deuteration degrees at the 2-position were 96% and 98% respectively, and the yields were 90% and 6% respectively. The reaction is expressed by the following scheme.

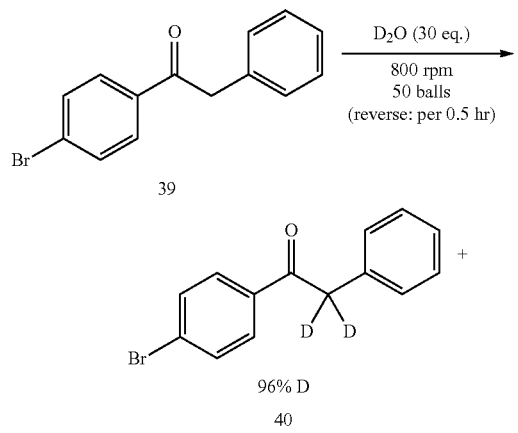

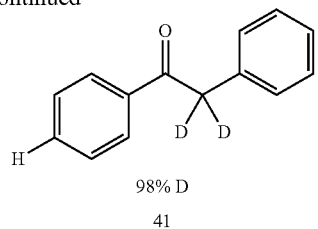

It was found from the results that when the rotation number of the balls was smaller, only the deuteration at the α-position of the ketone proceeded, and when the rotation number of the balls was larger, the compound deuterated at the α-position of the ketone was obtained with a high deuteration degree, but the reduction of the bromo group partially proceeded. Accordingly, it was understood that the extent of deuteration of an organic compound was able to be controlled by controlling the rotation number of the agitation medium, i.e., the mechanical energy.

INDUSTRIAL APPLICABILITY

According to the present invention, hydrogen or heavy hydrogens may be formed conveniently without the necessity of large-scale equipment, and hydrogen or heavy hydrogens may be collected in the form of gas or may be applied to hydrogenation (protiation, deuteration or tritiation) reaction.

Accordingly, the invention may be advantageously applied to a small-scale hydrogen or heavy hydrogen gas production apparatus and a simple hydrogenation (protiation, deuteration or tritiation) reaction apparatus for an organic compound.

The invention claimed is:
1. A process for producing a protiated, deuterated or tritiated organic compound, the process comprising mechanochemically reacting an organic compound (I) with water or heavy water in the presence of a catalyst metal whereby water or heavy water is converted to hydrogen or heavy hydrogen that protiate, deutrate, or tritiate the organic compound (I) to produce the protiated, deuterated, or tritiated organic compound (II), wherein the mechanochemically reacting is performed with a planetary ball mill, and wherein the catalyst metal comprises at least one selected from the group consisting of iron, iron(II) hydroxide, nickel, nickel(II) oxide, chromium, chromium(III) oxide and palladium.
2. The process of claim 1, wherein the organic compound comprises a halogen, and the protiated, deuterated or tritiated organic compound is a dehalogenated organic compound.
3. The process of claim 1, wherein the organic compound comprises a halogen, and the protiated, deuterated or tritiated organic compound is a dehalogenated organic compound.
4. The process of claim 1, wherein the organic compound comprises a halogen, and the protiated, deuterated or tritiated organic compound is a dehalogenated organic compound.
5. The process of claim 1, comprising mechanochemically reacting the organic compound with water.
6. The process of claim 1, comprising mechanochemically reacting the organic compound with heavy water.
7. The process of claim 1, wherein the organic compound is selected from the group consisting of ethynylbenzene, diphenylacetylene, phenylethylene, (E)-1,2-diphenylethylene, (Z)-1,2-diphenylethylene, 1,1-diphenylethylene, phenylaldehyde, methyl phenyl ketone, nitrobenzene, phenyl azide, chlorobenzene and phenyl methyl oxy benzene.

8. The process of claim 1, wherein the catalyst metal comprises palladium.

9. A process for protiating, deuterating or tritiating an organic compound, the process comprising mechanochemically reacting an organic compound (I) with water or heavy water in the presence of a catalyst metal whereby water or heavy water is converted to hydrogen or heavy hydrogen that protiate, deutrate, or tritiate the organic compound (I), wherein the mechanochemically reacting is performed with a planetary ball mill, and wherein the catalyst metal comprises at least one selected from the group consisting of iron, iron(II) hydroxide, nickel, nickel(II) oxide, chromium, chromium (III) oxide and palladium.

10. The process of claim 9, wherein the catalyst metal comprises palladium.

11. A process for dehalogenating an organic compound comprising a halogen, the process comprising mechanochemically reacting an organic compound comprising a halogen (I) with water or heavy water in the presence of a catalyst metal whereby water or heavy water is converted to hydrogen or heavy hydrogen that protiate, deutrate, or tritiate the organic compound (I) to produce the protiated, deuterated, or tritiated organic compound comprising a halogen (II), wherein the mechanochemically reacting is performed with a planetary ball mill, and wherein the catalyst metal comprises at least one selected from the group consisting of iron, iron(II) hydroxide, nickel, nickel(II) oxide, chromium, chromium (III) oxide and palladium.

12. The process of claim 11, wherein the organic compound comprising a halogen is polychlorinated biphenyl.

13. The process of claim 11, wherein the catalyst metal comprises stainless steel and palladium.

* * * * *